(12) United States Patent
Hanson et al.

(10) Patent No.: US 7,067,657 B2
(45) Date of Patent: Jun. 27, 2006

(54) THIAZOLOPYRIMIDINE DERIVATIVES AND USE THEREOF AS ANTAGONISTS OF THE $CX_3CR1$ RECEPTOR

(75) Inventors: Sverker Hanson, Södertälje (SE); Gunnar Nordvall, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 206 days.

(21) Appl. No.: 10/472,992

(22) PCT Filed: Mar. 26, 2002

(86) PCT No.: PCT/SE02/00599

§ 371 (c)(1),
(2), (4) Date: Sep. 25, 2003

(87) PCT Pub. No.: WO02/076990

PCT Pub. Date: Oct. 3, 2002

(65) Prior Publication Data

US 2004/0106628 A1    Jun. 3, 2004

(30) Foreign Application Priority Data

Mar. 27, 2001 (SE) .................................... 0101082

(51) Int. Cl.
C07D 513/04 (2006.01)
(52) U.S. Cl. .................................... 544/255
(58) Field of Classification Search ............. 514/260.1; 544/255
See application file for complete search history.

(56) References Cited

FOREIGN PATENT DOCUMENTS

WO    0009511    2/2000
WO    0158907    8/2001

OTHER PUBLICATIONS

Umehara H, Bloom ET, Okazaki T, Nagano Y, Yoshie O, Imai T, Arterioscler Thromb Vasc Biol. Jan. 2004; 24(1):34-40, Epub Sep. 11, 2003.*
Zujovic et al., "Fractalkine Modulates TNF-alpha Secretion and Neurotoxicity Induced by Microglial Activation," GLIA 29, 305-315 (2000).
Twining et al., "Spinal Fractalkine Induces Allodynia & Hyperalgesia," Society for Neuroscience 27, 732, Abstract No. 279.12 (2001).
Watkins et al., "Spinal Fractalkine: Key Player in Exaggerated Pain States," IASP Abstract No. 390-P24 (2002).
Verge et al., "Mapping Fractalkine and its Receptor (CX3CR1) in a Rat Model of Inflammatory Neuropathy," IASP Abstract No. 393-P27 (2002).
Volin et al., "Fractalkine: A Novel Angiogenic Chemokine in Rheumatoid Arthritis," Am. J. Pathology 159, 1521-1530 (2001).
Ruth et al., "Fractalkine, a Novel Chemokine in Rheumatoid Arthritis and in Rat Adjuvant-Induced Arthritis," Arthritis Rheum. 44, 1568-1581 (2001).
Soriano et al., "Mice Deficient in Fractalkine are less Susceptible to Cerebral Ischemia-Reperfusion Injury," J. Neuroimmunol. 125, 59-65 (2002).
Tarozzo et al., "Expression of Fractalkine and its Receptor, CX3CR1, in Response to Ischaemia-Reperfusion Brain Injury in the Rat," Eur. J. Neuroscience 15, 1663-1668 (2002).
Chapman et al., "Fractalkine Cleavage from Neuronal Membranes Represents an Acute Event in the Inflammatory Response to Excitotoxic Brain Damage," J. Neuroscience 20, 1-5 (2000).
Umehara et al., "Fractalkine and Vascular Injury," Trends Immunol. 22, 602-607 (2001).
Moatti et al., "Polymorphism in the Fractalkine Receptor CX3CR1 as a Genetic Risk Factor for Coronary Artery Disease," Blood 97, 1925-1928 (2001).
Balabanian et al., "CX3C Chemokine Fractalkine in Pulmonary Arterial Hypertension," Am. J. Respir. Crit. Care Med. 165, 1419-1425 (2002).

* cited by examiner

Primary Examiner—Thomas C. McKenzie
(74) Attorney, Agent, or Firm—Karen H. Kondrad

(57) ABSTRACT

Provided herein is a compound having the formula (Ia):

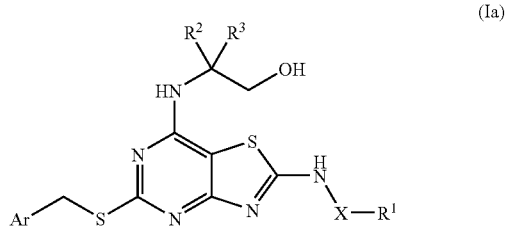

wherein said compounds are useful for the treatment or prophylaxis of neurodegenerative disorders, demyelinating disease and pain.

1 Claim, No Drawings

THIAZOLOPYRIMIDINE DERIVATIVES AND USE THEREOF AS ANTAGONISTS OF THE CX₃CR1 RECEPTOR

FIELD OF THE INVENTION

The present invention relates to the use of thiazolopyrimidine derivatives as antagonists of the $CX_3CR1$ receptor. Certain novel thiazolopyrimidine derivatives are also disclosed together with processes for their preparation, compositions containing them and their use in therapy.

BACKGROUND OF THE INVENTION

Chemokines play an important role in immune and inflammatory responses in various diseases and disorders, including asthma and allergic diseases, as well as autoimmune pathologies such as rheumatoid arthritis and atherosclerosis. These small secreted is molecules are a growing superfamily of 8–14 kDa proteins characterised by a conserved four cysteine motif. The chemokine superfamily can be divided into two:main groups exhibiting characteristic structural motifs, the Cys-X-Cys (C—X—C) and Cys-Cys (C—C) families. These two groups are distinguished on the basis of a single amino acid insertion between the NH-proximal pair of cysteine residues and sequence similarity.

The C—X—C chemokines include several potent chemoattractants and activators of, neutrophils such as interleukin-8 (CXCL8) and neutrophil-activating peptide 2 (CXCL7).

The C—C chemokines include potent chemoattractants of monocytes and lymphocytes but not neutrophils. Examples include human monocyte chemotactic proteins 1–3 (CCL2, CCL7 and CCL8), RANTES (CCL5), eotaxin (CCL11) and the macrophage inflammatory proteins 1α and 1β (CCL3 and CCL4).

There is also a third chemokine family based upon the structural motif Cys-X₃-Cys (C—X₃—C). This C—X₃—C family is distinguished from the C—X—C and C—C families on the basis of having a triple amino acid insertion between the NH-proximal pair of cysteine residues. $CX_3CL1$ (also known as fractalkine) is a potent chemoattractant and activator of microglia in the central nervous system as well as of monocytes, T cells, NK cells and mast cells.

Studies have demonstrated that the actions of the chemokines are mediated by subfamilies of G protein-coupled receptors. In particular, the actions of $CX_3CL1$ are mediated by the $CX_3CR1$ receptor.

WO 00/09511 discloses thiazolopyrimidine compounds that are useful as antagonists of receptors linked to the C—X—C and C—C chemokine families, particularly as antagonists of the CXCR2 receptor.

The present invention relates to a group of compounds that are partly within the generic scope of WO 00/09511 but which surprisingly display useful properties as antagonists of the $CX_3CR1$ receptor.

DISCLOSURE OF THE INVENTION

According to the present invention, there is provided the use of a compound of formula (I)

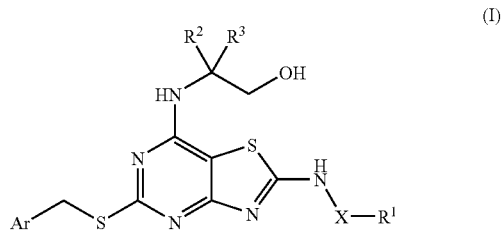

wherein:
$R^1$ represents hydrogen, $NR^4R^5$, $CONR^6R^7$ or a 4 to 7 membered saturated monoazacyclic ring optionally substituted by C1 to C6 alkyl or C1 to C6 alkyl-$OR^8$;
$R^2$ represents C3 to C7 alkyl, optionally substituted by $OR^9$ or $NR^{10}R^{11}$;
$R^3$ represents hydrogen or C1 to C7 alkyl, optionally substituted by $OR^{12}$ or $NR^{13}R^{14}$;
or $R^2$ and $R^3$ are joined together such that the group $R^2$—C—$R^3$ forms a C3 to C7 cycloalkyl group, optionally substituted by $OR^9$ or $NR^{10}R^{11}$;
Ar represents phenyl optionally substituted by one or more groups selected independently from halogen, C1 to C6 alkyl, C1 to C6 alkoxy, methylenedioxy, cyano, nitro, —$CO_2R^{15}$ or —$CONR^{16}R^{17}$; said alkyl group being optionally substituted by one or more fluorine atoms;
X represents a bond or C1 to C6 alkyl;
$R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ independently represent hydrogen or C1 to C6 alkyl;
or a pharmaceutically acceptable salt, enantiomer or racemate thereof, in the manufacture of a medicament, for the treatment or prophylaxis of diseases or conditions in which antagonism of the $CX_3CR1$ receptor is beneficial.

In one embodiment, $R^2$ represents C3 to C7 alkyl, optionally substituted by $OR^9$ or $NR^{10}R^{11}$; $R^3$ represents hydrogen or C1 to C7 alkyl, optionally substituted by $OR^{12}$ or $NR^{13}R^{14}$; and Ar represents phenyl optionally substituted by one or more groups selected independently from halogen and C1 to C6 alkoxy.

A more particular aspect of the invention provides the use of a compound of formula (I) or a pharmaceutically acceptable salt, enantiomer or racemate thereof, in the manufacture of a medicament, for the treatment or prophylaxis of neurodegenerative disorders, demyelinating disease or pain.

According to the invention, there is also provided a method of treating, or reducing the risk of, diseases or conditions in which antagonism of the $CX_3CR1$ receptor is beneficial which comprises administering to a person suffering from or at risk of, said disease or condition, a therapeutically effective amount of a compound of formula (I) or a pharmaceutically acceptable salt, enantiomer or racemate thereof.

More particularly, there is also provided a method of treating, or reducing the risk of, neurodegenerative disorders, demyelinating disease or pain in a person suffering from or at risk of, said disease or condition, wherein the method comprises administering to the person a therapeutically effective amount of a compound of formula (I) or a pharmaceutically acceptable salt, enantiomer or racemate thereof.

In another aspect the invention provides a pharmaceutical formulation comprising a therapeutically effective amount of a compound of formula (I), or a pharmaceutically acceptable salt, enantiomer or racemate thereof, in admixture with a pharmaceutically acceptable adjuvant, diluent or carrier, for use in the treatment or prophylaxis of diseases or conditions in which antagonism of the $CX_3CR1$ receptor is beneficial.

In another more particular aspect the invention provides a pharmaceutical formulation comprising a therapeutically effective amount of a compound of formula (I), or a pharmaceutically acceptable salt, enantiomer or racemate thereof, in admixture with a pharmaceutically acceptable adjuvant, diluent or carrier, for use in the treatment or prophylaxis of neurodegenerative disorders, demyelinating disease or pain.

In one embodiment, $R^1$ represents hydrogen and X represents a bond.

In a second embodiment, $R^1$ represents $CONR^4R^5$ and X represents C1 to C6 alkyl. More preferably, $R^1$ represents $CONH_2$ and X represents C1 to C6 alkyl. Even more preferably, $R^1$ represents $CONH_2$ and X represents $CH_2$.

In a further embodiment, $R^1$ represents piperidinyl, optionally substituted by C1 to C6 alkyl More preferably, $R^1$ represents 4-piperidinyl. Even more preferably, $R^1$ represents 4-piperidinyl and X represents a bond.

It is preferred that $R^2$ represents C3 to C7 alkyl.

It is preferred that $R^3$ represents hydrogen or C1 to C7 alkyl. More preferably, $R^3$ represents hydrogen.

Compounds of formula (I) wherein Ar represents a phenyl ring substituted by halogen, C1 to C6 alkoxy, $-CO_2R^{15}$ or $-CONR^{16}R^{17}$ are also preferred.

Unless otherwise indicated, the term "C1 to C7 alkyl" referred to herein denotes a straight or branched chain alkyl group having from 1 to 7 carbon atoms and/or a cyclic alkyl group having from 3 to 7 carbon atoms. Examples of such groups include methyl, ethyl, 1-propyl, 2-propyl, n-butyl, iso-butyl, tert-butyl, pentyl, hexyl, cyclopropyl, cyclopropylmethyl, cyclopentyl, methylcyclopentyl, cyclopentylmethyl and cyclohexyl.

The terms "C1 to C6 alkyl" and "C3 to C7 alkyl" are to be interpreted analogously.

Unless otherwise indicated, the term "C1 to C6 alkoxy" referred to herein denotes a straight or branched chain alkoxy group having from 1 to 6 carbon atoms; Examples of such groups include methoxy, ethoxy, 1-propoxy, 2-propoxy and tert-butoxy.

Unless otherwise indicated, the term "halogen" referred to herein denotes fluoro, chloro, bromo and iodo.

Examples of a 4 to 7 membered saturated monoazacyclic ring include pyrrolidine, piperidine, piperazine and perhydroazepine.

Certain compounds of formula (I) are novel. Therefore a further aspect of the invention provides a compound of formula (Ia)

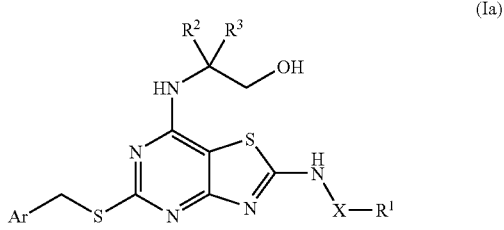

wherein:
$R^1$ represents hydrogen, $NR^4R^5$, $CONR^6R^7$ or a 4 to 7 membered saturated monoazacyclic ring optionally substituted by C1 to C6 alkyl or C1 to C6 alkyl-$OR^8$;
$R^2$ represents C3 to C7 alkyl, optionally substituted by $OR^9$ or $NR^{10}R^{11}$;
$R^3$ represents hydrogen or C1 to C7 alkyl, optionally substituted by $OR^{12}$ or $NR^{13}R^{14}$;
or $R^2$ and $R^3$ are joined together such that the group $R^2$—C—$R^3$ forms a C3 to C7 cycloalkyl group, optionally substituted by $OR^9$ or $NR^{10}R^{11}$;
Ar represents phenyl optionally substituted by one or more groups selected. independently from halogen, C1 to C6 alkyl C1 to C6 alkoxy, methylenedioxy, cyano, nitro, $-CO_2R^{15}$ or $-CONR^{16}R^{17}$; said alkyl group being optionally substituted by one or more fluorine atoms;
X represents a bond or C1 to C6 alkyl;
$R^4, R^5, R^6, R^7, R^8, R^9, R^{10}, R^{11}, R^{12}, R^{13}, R^{14}, R^{15}, R^{16}$ and $R^{17}$ independently represent hydrogen or C1 to C6 alkyl;
or a pharmaceutically acceptable salt, enantiomer or racemate thereof;
with the proviso that when $R^1$ and $R^3$ each represent hydrogen and $R^2$ represents iso-butyl Ar does not represent unsubstituted phenyl or 2,3-difluorophenyl.

Particular compounds of formula (Ia) include:
(±)-2-(2-amino-5-phenylmethylthio-thiazolo[4,5-d]pyrimidin-7-ylamino)-3-methyl-butan-1-ol;
(±)-2-(2-amino-5-phenylmethylthio-thiazolo[4,5-d]pyrimidin-7-ylamino)-hexan-1-ol;
(R)-2-[5-phenylmethylthio-7-(1-hydroxymethyl-3-methyl-butylamino)-thiazolo[4,5-d]pyrimidin-2-ylamino]-acetamide;
(R)-2-[5-phenylmethylthio-2-(piperidin4-ylamino)-thiazolo[4,5-d]pyrimidin-7-ylamino]-4-methyl-pentan-1-ol;
(R)-2-[2-amino-5-(2-fluorophenylmethylthio)-thiazolo[4,5-d]pyrimidin-7-ylamino]-4-methyl-pentan-1-ol;
(R)-2-[2-amino-5-(2-chlorophenylmethylthio)-thiazolo[4,5-d]pyrimidin-7-ylamino]-4-methyl-pentan-1-ol;
(R)-2-[2-amino-5-(2-bromophenylmethylthio)-thiazolo[4,5-d]pyrimidin-7-ylamino]-4-methyl-pentan-1-ol;
(R)-2-[2-amino-5-(3-bromophenylmethylthio)-thiazolo[4,5-d]pyrimidin-7-ylamino]-4-methyl-pentan-1-ol;
(R)-2-[2-amino-5-(4-bromophenylmethylthio)-thiazolo[4,5-d]pyrimidin-7-ylamino]-4-methyl-pentan-1-ol;
(R)-2-[2-amino-5-(2-iodophenylmethylthio)-thiazolo[4,5-d]pyrimidin-7-ylamino]-4-methyl-pentan-1-ol;
(R)-2-[2-amino-5-(2,4-difluorophenylmethylthio)-thiazolo[4,5-d]pyrimidin-7-ylamino]-4-methyl-pentan-1-ol;
(R)-2-[2-amino-5-(2,5-difluorophenylmethylthio)-thiazolo[4,5-d]pyrimidin-7-ylamino]-4-methyl-pentan-1-ol;
(R)-2-[2-amino-5-(2,6-difluorophenylmethylthio)-thiazolo[4,5-d]pyrimidin-7-ylamino]-4-methyl-pentan-1-ol;
(R)-2-[2-amino-5-(3,4-difluorophenylmethylthio)-thiazolo[4,5-d]pyrimidin-7-ylamino]-4-methyl-pentan-1-ol;
(R)-2-[2-amino-5-(3,5-difluorophenylmethylthio)-thiazolo[4,5-d]pyrimidin-7-ylamino]-4-methyl-pentan-1-ol;
(R)-2-[2-amino-5-(3-chloro-2-fluorophenylmethylthio)-thiazolo[4,5-d]pyrimidin-7-ylamino]-4-methyl-pentan-1-ol;
(R)-2-[2-amino-5-(2-chloro-6-fluorophenylmethylthio)-thiazolo[4,5-d]pyrimidin-7-ylamino]-4-methyl-pentan-1-ol;
(R)-2-[2-amino-5-(4-bromo-2-fluorophenylmethylthio)-thiazolo[4,5-d]pyrimidin-7-ylamino]-4-methyl-pentan-1-ol;

(R)-2-[2-amino-5-(2-bromo-5-fluorophenylmethylthio)-thiazolo[4,5-d]pyrimidin-7-ylamino]-4-methyl-pentan-1-ol;

(R)-2-[2-amino-5-(2,3-dichlorophenylmethylthio)-thiazolo[4,5-d]pyrimidin-7-ylamino]-4-methyl-pentan-1ol;

(R)-2-[2-amino-5-(2-chloro-4,5-methylenedioxyphenylmethylthio)-thiazolo[4,5-d]pyrimidin-7-ylamino]-4-methyl-pentan-1-ol;

(R)-2-[2-amino-5-(2-methoxyphenylmethylthio)-thiazolo[4,5-d]pyrimidin-7-ylamino]-4-methyl-pentan-1-ol;

(R)-2-[2-amino-5-(3-methoxyphenylmethylthio)-thiazolo[4,5-d]pyrimidin-7-ylamino]-4-methyl-pentan-1-ol;

(R)-2-[2-amino-5-(4-methoxyphenylmethylthio)-thiazolo[4,5-d]pyrimidin-7-ylamino]-4-methyl-pentan-1-ol;

(R)-2-[2-amino-5-(2-fluoro-3-methylphenylmethylthio)-thiazolo[4,5-d]pyrimidin-7-ylamino]methyl-pentan-1-ol;

(R)-2-[2-amino-5-(2-fluoro-3-trifluoromethylphenylmethylthio)-thiazolo[4,5-d]pyrimidin-7-ylamino]-4-methyl-pentan-1-ol;

(R)-2-[2-amino-5-(2-bromo-5-methylphenylmethylthio)-thiazolo[4,5-d]pyrimidin-7-ylamino]-4-methyl-pentan-1-ol;

(R)-2-[2-amino-5-(3-methoxycarbonylphenylmethylthio)-thiazolo[4,5-d]pyrimidin-7-ylamino]-4-methyl-pentan-1-ol;

(R)-2-[2-amino-5-(4-trifluoromethylphenylmethylthio)-thiazolo[4,5-d]pyrimidin-7-ylamino]-4-methyl-pentan-1-ol;

(R)-2-[2-amino-5-(2-trifluoromethylphenylmethylthio)-thiazolo[4,5-d]pyrimidin-7-ylamino]-4-methyl-pentan-1-ol;

(R)-2-[2-amino-5-(4-cyanophenylmethylthio)-thiazolo[4,5-d]pyrimidin-7-ylamino]-4-methyl-pentan-1-ol;

(R)-2-[2-amino-5-(4-methylphenylmethylthio)-thiazolo[4,5-d]pyrimidin-7-ylamino]-4-methyl-pentan-1-ol;

(R)-2-[2-amino-5-(3-methylphenylmethylthio)-thiazolo[4,5-d]pyrimidin-7-ylamino]-4-methyl-pentan-1-ol;

(R)-2-[2-amino-5-(2-cyanophenylmethylthio)-thiazolo[4,5-d]pyrimidin-7-ylamino]-4-methyl-pentan-1-ol;

(R)-2-[2-amino-5-(2-methylphenylmethylthio)-thiazolo[4,5-d]pyrimidin-7-ylamino]-4-methyl-pentan-1-ol;

(R)-2-[2-amino-5-(3-trifluoromethylphenylmethylthio)-thiazolo[4,5-d]pyrimidin-7-ylamino]-4-methyl-pentan-1-ol;

(R)-2-[2-amino-5-(3-cyanophenylmethylthio)-thiazolo[4,5-d]pyrimidin-7-ylamino]-4-methyl-pentan-1-ol;

(R)-2-[2-amino-5-(3-methyl-2-nitrophenylmethylthio)-thiazolo[4,5-d]pyrimidin-7-ylamino]-4-methyl-pentan-1-ol;

N-(2-amino-5-phenylmethylthio-thiazolo[4,5-d]pyrimidin-7-yl)-1-hydroxymethyl-cyclopentylamine;

(±)-2-[2-amino-5-(2,3-difluorophenylmethylthio)-thiazolo[4,5-d]pyrimidin-7-ylamino]-hexan-1-ol;

and pharmaceutically acceptable salts, enantiomers or racemates thereof.

According to the invention, we further provide a process for the preparation of compounds of formula (Ia), or a pharmaceutically acceptable salt, enantiomer or racemate thereof which comprises:

(a) reaction of a compound of formula (II)

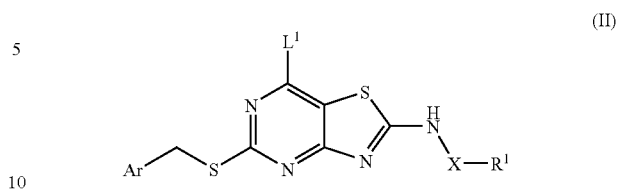

wherein $R^1$ Ar and X are as defined in formula (Ia) and $L^1$ represents a leaving group;
with a compound of formula (III) or a salt thereof

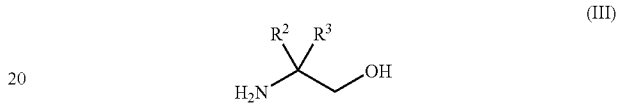

wherein $R^2$ and $R^3$ are as defined in formula (Ia); or
(b) reaction of a compound of formula (IV)

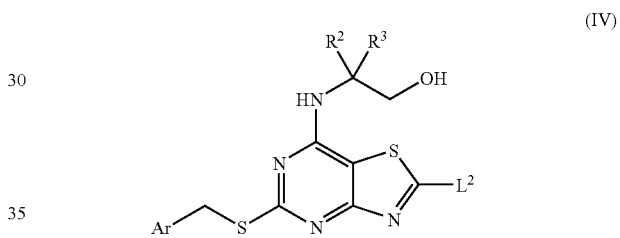

wherein $R^2$, $R^3$ and Ar are as defined in formula (Ia) and $L^2$ represents a leaving group;
with a compound of formula (V) or a salt thereof

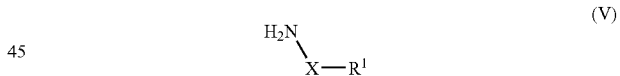

wherein $R^1$ and X are as defined in formula (Ia);
and where necessary converting the resultant compound of formula (Ia), or another salt thereof, into a pharmaceutically acceptable salt thereof, or converting the resultant compound of formula (Ia) into a further compound of formula (Ia); and where desired converting the resultant compound of formula (Ia) into an optical isomer thereof.

In processes (a) and (b), the reactants (I) and (III) or (IV) and (V) are coupled together in a suitable inert organic solvent such as tetrahydrofuran, acetonitrile or dichloromethane. The reaction is optionally performed in the presence of an added base. This base may be an organic base such as triethyl amine or an inorganic base such as potassium carbonate. The reaction is conducted at a suitable temperature, normally between room temperature and the boiling point of the solvent,-but optionally at higher temperatures if a sealed reaction vessel is used. The reaction is generally continued for a period of about one hour to one week, or until analysis indicates that formation of the required product is complete. Preferred leaving groups $L^1$ and $L^2$ are halogen, particularly chloro or bromo.

It will be apparent to a person skilled in the art that in the above processes it may be desirable or necessary to protect an amine, hydroxyl or other potentially reactive group. Suitable protecting groups and details of processes for adding and removing such groups may be found by reference to the standard text "Protective Groups in Organic Synthesis", 3rd Edition (1999) by Greene and Wuts. In one preferred embodiment, amine groups are protected as carbamate derivatives, for example, as t-butyloxycarbamates.

The present invention includes compounds of formula (Ia) in the form of salts, in particular acid addition salts. Suitable salts include those formed with both organic and inorganic acids. Such acid addition salts will normally be pharmaceutically acceptable although salts of non-pharmaceutically acceptable acids maybe of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (Ia) may be formed by reacting the free base, or a salt, enantiomer or racemate thereof, with one or more equivalents of the appropriate acid. The reaction may be carried out in a solvent or medium in which the salt is insoluble or in a solvent in which the salt is soluble, for example, water, dioxan, ethanol, tetrahydrofuran or diethyl ether, or a mixture of solvents, which may be removed in vacuo or by freeze drying. The reaction may also be a metathetical process or it may be carried out on an ion exchange resin.

Compounds of formulae (II) and (IV) are either known from WO 00/09511 or may be prepared using known methods that will be readily apparent to the man skilled in the art.

Compounds of formulae (III) and (V) are either commercially available, or known in the literature, or may be prepared using known methods that will be readily apparent to the man skilled in the art.

Intermediate compounds may be used as such or in protected form. Protecting groups and details of processes for their removal may be found by reference to the standard text "Protective Groups in Organic Synthesis", 3rd Edition (1999) by Greene and Wuts.

The compounds of the invention and intermediates thereto may be isolated from their reaction mixtures and, if necessary further purified, by using standard techniques.

The compounds of formula (Ia) may exist in enantiomeric forms. Therefore, all enantiomers, diastereomers, racemates and mixtures thereof are included within the scope of the invention. The various optical isomers may be isolated by separation of a racemic mixture of the compounds using conventional techniques, for example, fractional crystallisation, or HPLC. Alternatively, the various optical isomers may be prepared directly using optically active starting materials.

Intermediate compounds may also exist in enantiomeric forms and maybe used as purified enantiomers, diastereomers, racemates or mixtures.

The compounds of formula (Ia), and their pharmaceutically acceptable salts, enantiomers and racemates, are useful because they possess pharmacological activity as antagonists of the $CX_3CR1$ receptor.

The compounds of formulae (I) and (Ia) and their pharmaceutically acceptable salts, enantiomers and racemates are indicated for use in the treatment or prophylaxis of diseases or conditions in which modulation of activity at the $CX_3CR1$ receptor is desirable. In particular, the compounds are indicated for use in the treatment of neurodegenerative disorders or demyelinating disease in mammals including man. The compounds are also indicated to be useful in the treatment of pain.

Conditions that may be specifically mentioned are: neurodegenerative diseases and dementia disorders, for example, Alzheimer's disease, amyotrophic lateral sclerosis and other motor neuron diseases, Creutzfeldt-Jacob's disease and other prion diseases, HIV encephalopathy, Huntington's disease, frontotemporal dementia, Lewy body dementia and vascular dementia; polyneuropathies, for example, Guillain-Barré syndrome, chronic inflammatory demyelinating polyradiculoneuropathy, multifocal motor neuropathy and plexopathies; CNS demyelination, for example, acute disseminated/haemorrhagic encephalomyelitis and subacute sclerosing panencephalitis; neuromuscular disorders, for example, myasthenia gravis and Lambert-Eaton syndrome; spinal disorders, for example, tropical spastic paraparesis and stiff-man syndrome; paraneoplastic syndromes, for example, cerebellar degeneration and encephalomyelitis; CNS trauma; and migraine.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formulae (I) or (Ia), and pharmaceutically acceptable derivatives thereof, may be used on their own, or in the form of appropriate pharmaceutical compositions in which the compound or derivative is in admixture with a pharmaceutically acceptable adjuvant, diluent or carrier. Administration may be by, but is not limited to, enteral (including oral, sublingual or rectal), intranasal, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formulae (I) or (Ia), or a pharmaceutically acceptable salt, enantiomer or racemate thereof.

There is also provided a process for the preparation of such a pharmaceutical composition that is comprises mixing the ingredients.

The invention is illustrated, but in no way limited, by the following examples:

In the Examples, the nuclear magnetic resonance (NMR) spectra were recorded on a Varian Gemini 7 Tesla 300MHz instrument, or a Bruker Avance 400 MHz instrument using the solvent indicated. Chemical shifts are given in ppm down- and upfield from tetramethylsilane (TMS). Resonance multiplicities are denoted s, d, t, m, br and app for singlet, doublet, triplet, multiplet, broad and apparent, respectively. The mass spectrometry (MS) spectra were recorded on a Finnigan SSQ7000 TSP or a Finnigan SSQ710 DI/EI instrument, or on a single quadropole mass spectrometer, ZMD (Waters), using an electrospray ion source operated in a positive mode. The ion spray voltage was +3 kV and the mass spectrometer was scanned from m/z 100–900 with a scan time of 0.85 s. LC-MS was obtained with a Waters 2790 LC-system equipped with a Waters Xterra™ MS $C_8$ (2.5 μm×30 mm) column, a Waters 996 photodiode array detector and a Micromass ZMD. High pressure liquid chromatography (HPLC) assays were performed using a Hewlett Packard 1100 Series HPLC system equipped with a Zorbax SB-$C_8$ (4.6 mm×15 cm) column. Preparative high pressure liquid chromatography (Prep HPLC) separations were performed on an automated Gilson (model 170) using an x-tera $C_{18}$ (19 mm×30 cm) column. Column chromatography was performed using silica gel 60 (230–400 mesh ASTM, Merck) and thin layer chromatography (TLC) was performed on TLC precoated plates, silica gel 60 $F_{254}$ (Merck).

EXAMPLE 1

(±)-2-(2-Amino-5-phenylmethylthio-thiazolo[4,5-d]pyrimidin-7-ylamino)-3-methyl-butan-1-ol 5-Phenylmethylthio-7-chloro-thiazolo[4,5-d]pyrimidin-2-ylamine (WO 00/09511) (100 mg, 0.32 mmol) and DL-2-amino-3-methyl-1-butanol (253 μL, 2.3 mmol) were suspended in anhydrous tetrahydrofaran (4 mL) and the reaction tube was capped. The solution was heated at 100° C. for 24 hours and was then allowed to cool down to room temperature. The solvent was evaporated in vacuo and the crude product was flash chromatographed on silica (eluent—ammonia:ethanol:dichloromethane, 1:8:91) followed by a second chromatography (gradient eluent—ammonia ethyl acetate: dichloromethane, 1:59:40 to 1:99:0) resulting in 29 mg (24% yield) of the title compound as a white solid.

$^1$H NMR (d$_4$-MeOH) δ0.91 (d, 3H), 0.95 (d, 3H), 1.91–2.01 (m, 1H), 3.60–3.71 (m, 2H), 4.11–4.18 (m, 1H), 4.35 (d, 1H), 4.43 (d, 1H), 7.17–7.31 (m, 3H), 7.41 (br d, 2H); MS DI/EI$^m$/z (relative % intensity) 375 (M$^+$, 81), 342 (20), 256 (12), 91 (100), 65 (12).

EXAMPLE 2

(±)-2-(2-Amino-5-phenylmethylthio-thiazolo[4,5-d]pyrimidin-7-ylamino)-hexan-1-ol 5-Phenylmethylthio-7-chloro-thiazolo[4,5-d]pyrimidin-2-ylamin (100 mg, 0.32 mmol), DL-2-amino-1-hexanol (295 μL, 2.3 mmol) and potassium carbonate (124 mg, 0.90 mmol) were heated for 24 hours as in Example 1. The solution was filtered and the solvent was evaporated. The crude product was flash chromatographed on silica (gradient eluent—ammonia:ethylacetate:dichloromethane, 1:69:30 to 1:99:0) resulting in 22 mg (17% yield) of the title compound as a yellow solid.

$^1$H NMR (d$_4$-MeOH) δ0.88 (m, 3H), 1.22–1.42 (m, 4H), 1.44–1.59 (m, 1H), 1.60–1.72 (m, 1H), 3.52–3.63 (m, 2H), 4.28–4.37 (m, 1H), overlapping with 4.35 (d, 1H)), 4.45 (d, 1H), 7.15–7.36 (m, 3H), 7.41 (br d, 2H);

MS TSP (+ve) 390 (M+1).

EXAMPLE 3

(R)-2-[5-Phenylmethylthio-7-(1-hydroxymethyl-3-methyl-butylamino)-thiazolo[4,5-d]pyrimidin-2-ylamino]-acetamide (a) (R)-2-(5-Phenylmethylthio-2-bromo-thiazolo[4,5-d]pyrimidin-7-ylamino)-4-methyl-pentan-1-ol To a suspension of (R)-2-(2-amino-5-phenylmethylthio-thiazolo[4,5-d]pyrimidin-7-ylamino)-4-methyl-pentan-1-ol (WO 00/09511) (131 mg, 0.34 mmol) in bromoform (6 mL) and anhydrous acetonitrile (2.5 mL), isoamylnitrite (158 μL, 1.2 mmol) was added. The mixture was heated at 60° C. under a nitrogen atmosphere for 30 minutes followed by evaporation of the solvent. The crude, red solid was flash chromatographed on silica (eluent—ethyl acetate:dichloromethane, 10:90) and the product was dried in vacuo at 50° C. overnight, resulting in 61 mg (40% yield) of the title compound as a brown solid.

$^1$H NMR (d$_6$-DMSO) δ0.83 (d, 3H), 0.87 (d, 3H), 1.34–1.51 (m, 2H), 1.53–1.65 (m, 1H), 3.38–3.47 (m, 2H), 4.29–4.44 (m, 1H) overlapping with 4.35 (d, 1H) and 4.40 (d, 1H), 4.78 (bs, 1H), 7.21–7.34 (m, 3H), 7.43 (br d, 2H), 8.05 (d, 1H);

MS DI/EI $^m$/z (relative % intensity) 452, 454 (M$^+$, 36), 91 (100), 65 (12).

(b) (R)-2-[5-Phenylmethylthio-7-(1-hydroxymethyl-3-methyl-butylamino)-thiazolo[4,5-d]pyrimidin-2-ylamino]-acetamide The product from step (a) (20 mg, 44 μmol) and glycinamide hydrochloride (12.2 mg, 110 μmol) were dissolved in anhydrous acetonitrile (3 mL) and dichloromethane (1 mL). The solution was stirred under a nitrogen atmosphere at room temperature for 18 hours and then 3 equivalents of triethylamine were added. After 24 hours, another equivalent of triethylamine was added and the temperature was raised to 75° C. for 24 hours. The solution was cooled and the solvent was evaporated. The crude solid was flash chromatographed on silica (eluent—ammonia:ethyl acetate:ethanol, 0.5:10:89.5). After drying in vacuo at 45° C. overnight, 6 mg (47% yield) of the title compound was obtained as a white solid.

$^1$H NMR (d$_4$-MeOH) δ0.90 (d, 3H), 0.93 (d, 3H), 1.40–1.48 (m, 1H), 1.49–1.58 (m, 1H), 1.62–1.74 (m, 1H), 3.49–3.61 (m, 2H), 4.14 (s, 2H), 4.38 (d, 1H), 4.42–4.52 (m, 1H) overlapping with 4.44 (d, 1H), 7.17–7.31 (m, 3H), 7.41 (br d, 2H);

MS TSP (+ve) 447 (M+1).

EXAMPLE 4

(R)-2-[5-Phenylmethylthio-2-(piperidin-4-ylamino)-thiazolo[4,5-d]pyrimidin-7-ylamino]-4-methyl-pentan-1-ol (a) 4(5-Phenylmethylthio-7-chloro-thiazolo[4,5-d]pyrimidin-2-ylamino)-piperidine-1-carboxylic acid tert-butyl ester 5-Phenylmethylthio-2-bromo-7-chloro-thiazolo[4,5-d]pyrimidine (WO 00/09511) (525 mg, 1.4 mmol), 4-amino-1-N-Boc-piperidine (339 mg, 1.7 mmol) and triethylamine (196 μL, 1.4 mmol) were dissolved in anhydrous acetonitrile (15 mL) and the mixture was stirred under a nitrogen atmosphere at 35° C. for 24 hours. The mixture was filtered and the remaining solid was washed with acetonitrile. After drying in air for 48 hours, 396 mg (57% yield) of the title compound was obtained as a white solid.

$^1$H NMR ($d_6$-DMSO) δ1.35–1.50 (m, 11H), 1.93–2.03 (m, 2H), 2.90–3.04 (m, 2H), 3.82–3.92 (m, 2H), 4.08 (br s, 1H), 4.42 (s, 2H), 7.22–7.36 (m, 3H), 7.44 (br d, 2H), 9.36 (br s, 1H);

MS TSP (+ve) 492 (M+1), 392 (M+1-Boc).

(b) (R)-4-[5-Phenylmethylthio-7-(1-hydroxymethyl-3-methyl-butylamino)-thiazolo[4,5-d]pyrimidin-2-ylamino]-piperidine-1-carboxylic acid tert-butyl ester The product from step (a) (50 mg, 0.1 mmol) and D-leucinol (60 mg, 0.5 mmol) were dissolved in anhydrous tetrahydrofuran (3 mL). The solution was heated in a capped reaction tube at 100° C. for 7 days. The crude product was flash chromatographed on silica (gradient eluent—ammonia:ethyl acetate:chloroform, 1:9:90 to 1:49:50). The product was dried in vacuo at room temperature resulting in 44 mg (76% yield) of the title compound as a white solid.

MS TSP (+ve) 573 (M+1).

(c) (R)-2-[5-Phenylmethylthio-2-(piperidin4-ylamino)-thiazolo[4,5-d]pyrimidin-7-ylamino]-4-methyl-pentan-1-ol The product from step (b) (40 mg, 70 µmol) was dissolved in anhydrous dichloromethane (2.5 mL) and trifluoroacetic acid (269 µL, 3.5 mmol) was added. The mixture was stirred at room temperature for two hours. 1M Aqueous potassium carbonate (3.5 mL) followed by 0.1M aqueous sodium hydroxide (1 mL) were added and the product was extracted twice with dichloromethane. The precipitate which formed was filtered off, washed with dichloromethane and dried in vacuo at 40° C. overnight resulting in 24 mg (73% yield) of the title compound as an off-white solid.

$^1$H NMR ($d_4$-MeOH) δ0.90 (d, 3H), 0.93 (d, 3H), 1.38–1.57 (m, 4H), 1.62–1.75 (m, 1H), 2.05–2.14 (m, 2H), 2.73 (m, 2H), 3.06–3.14 (m, 2H), 3.54 (m, 2H), 3.84–3.96 (m, 1H), 4.38–4.50 (m, 1H) overlapping with 4.28 (d, 1H) and 4.44 (d, 1H), 7.17–7.31(m, 3H), 7.40 (br d, 2H);

MS TSP (+ve) 473 (M+1).

EXAMPLE 5

(R)-2-[2-Amino-5-(2-fluorophenylmethylthio)-thiazolo[4,5-d]pyrimidin-7-ylamino]-4-methyl-pentan-1-ol

(a) (R)-2-[2-Amino-5-mercapto-thiazolo[4,5-d]pyrimidin-7-ylamino]-4-methyl-pentan-1-ol Liquid ammonia (140 mL) was condensed into a 250 mL flask (dry ice/acetone cooling) is and (R)-2-(2-amino-5-phenylmethylthio-thiazolo[4,5-d]pyrimidin-7-ylamino)-4-methyl-pentan-1-ol (WO 00/09511) (2.77 g, 7.11 mmol) was added in three portions. To the clear yellow solution was added an excess of sodium metal in small pieces, until a blue colour persisted. When the blue colour had remained for 25 seconds, solid NH$_4$Cl was added to quench the reaction. The NH$_3$ solvent was removed (N$_2$), and the remains were dissolved in H$_2$O (ca 70 mL), the mixture filtered, and the resulting clear solution neutralized to pH ca 7 with dilute HCl. The precipitated solid was filtered, washed with H$_2$O and CH$_3$CN, and dried at 40° C. under vacuum overnight to give 1.98 g (93%) of a light yellow solid.

MS 300 (M+1).

(b) (R)-2-[2-Amino-5-(2-fluorophenylmethylthio)-thiazolo[4,5-d]pyrimidin-7-ylamino]-4-methyl-pentan-1-ol The product from step (a) (20 mg, 67 µmol) was suspended in dimethyl sulphoxide (450 µL) and Hunig's base (13 µL, 74 µmol) was added. 2-Fluorobenzyl bromide (8.0 µL, 67 µmol) was quickly added to the stirred solution. The reaction was stirred for 60 minutes to give a homogeneous solution The crude solution was diluted to 1 mL with acetonitrile and chromatographed on a reverse phase column using a gradient (40–70% acetonitrile) to give the title compound as a white solid (17 mg, 61% yield).

MS408(M+1).

The compounds of Examples 6 to 38 were prepared using the general method of Example but replacing 2-fluorobenzyl bromide with the appropriately substituted benzyl halide.

EXAMPLE 6

(R)-2-[2-Amino-5-(2-chlorophenylmethylthio)-thiazolo[4,5-d]pyrimidin-7-ylamino]-4-methyl-pentan-1-ol White solid (13 mg, 48% yield). MS 424 (M+1).

EXAMPLE 7

(R)-2-[2-Amino-5-(2-bromophenylmethylthio)-thiazolo[4,5-d]pyrimidin-7-ylamino]-4-methyl-pentan-1-ol Off-white solid (130 mg, 41% yield). MS 468, 470 (M+1).

EXAMPLE 8

(R)-2-[2-Amino-5-(3-bromophenylmethylthio)-thiazolo[4,5-d]pyrimidin-7-ylamino]-4-methyl-pentan-1-ol White solid (19 mg, 61% yield). MS 468, 470 (M+1).

EXAMPLE 9

(R)-2-[2-Amino-5-(4-bromophenylmethylthio)-thiazolo[4,5-d]pyrimidin-7-ylamino]-4-methyl-pentan-1-ol White solid (18 mg, 57% yield). MS 468, 470 (M+1).

EXAMPLE 10

(R)-2-[2-Amino-5-(2-iodophenylmethylthio)-thiazolo[4,5-d]pyrimidin-7-ylamino]-4-methyl-pentan-1-ol White solid (19 mg, 55% yield). MS 516 (M+1).

EXAMPLE 11

(R)-2-[2-Amino-5-(2,4-difluorophenylmethylthio)-thiazolo[4,5-d]pyrimidin-7-ylamino]-4-methyl-pentan-1-ol White solid (15 mg, 51% yield). MS 426 (M+1).

EXAMPLE 12

(R)-2-[2-Amino-5-(2,5-difluorophenylmethylthio)-thiazolo[4,5-d]pyrimidin-7-ylamino]-4-methyl-pentan-1-ol White solid (20 mg, 69% yield). MS 426 (M+1).

EXAMPLE 13

(R)-2-[2-Amino-5-(2,6-difluorophenylmethylthio)-thiazolo[4,5-d]pyrimidin-7-ylamino]-4-methyl-pentan-1-ol White solid (18 mg, 43% yield). MS 426 (M+1).

EXAMPLE 14

(R)-2-[2-Amino-5-(3,4-difluorophenylmethylthio)-thiazolo[4,5-d]pyrimidin-7-ylamino]-4-methyl-pentan-1-ol White solid (14 mg, 48% yield). MS 426 (M+1).

EXAMPLE 15

(R)-2-[2-Amino-5-(3,5-difluorophenylmethylthio)-thiazolo[4,5-d]pyrimidin-7-ylamino]-4-methyl-pentan-1-ol White solid (13 mg, 46% yield). MS 426 (M+1).

EXAMPLE 16

(R)-2-[2-Amino-5-(3-chloro-2-fluorophenylmethylthio)-thiazolo[4,5-d]pyrimidin-7-ylamino]-4-methyl-pentan-1-ol White solid (18 mg, 60% yield). MS 442 (M+1).

EXAMPLE 17

(R)-2-[2-Amino-5-(2-chloro-6-fluorophenylmethylthio)-thiazolo[4,5-d]pyrimidin-7-ylamino]-4-methyl-pentan-1-ol White solid (18 mg, 56% yield). MS 442 (M+1).

EXAMPLE 18

(R)-2-[2-Amino-5-(4-bromo-2-fluorophenylmethylthio)-thiazolo[4,5-d]pyrimidin-7-ylamino]-4-methyl-pentan-1-ol White solid (18 mg, 54% yield). MS 486, 488 (M+1).

EXAMPLE 19

(R)-2-[2-Amino-5-(2-bromo-5-fluorophenylmethylthio)-thiazolo[4,5-d]pyrimidin-7-ylamino]-4-methyl-pentan-1-ol White solid (20 mg, 61% yield). MS 486, 488 (M+1).

EXAMPLE 20

(R)-2-[2-Amino-5-(2,3-dichlorophenylmethylthio)-thiazolo[4,5-d]pyrimidin-7-ylamino]-4-methyl-pentan-1-ol White solid (14 mg, 45% yield). MS 458 (M+1).

EXAMPLE 21

(R)-2-[2-Amino-5-(2-chloro-4,5-methylenedioxyphenylmethylthio)-thiazolo[4,5-d]pyrimidin-7-ylamino]-4-methyl-pentan-1-ol White solid (14 mg, 44% yield). MS 468 (M+1).

EXAMPLE 22

(R)-2-[2-Amino-5-(2-methoxyphenylmethylthio)-thiazolo[4,5-d]pyrimidin-7-ylamino]-4-methyl-pentan-1-ol White solid (15 mg, 54% yield). MS 420 (M+1).

EXAMPLE 23

(R)-2-[2-Amino-5-(3-methoxyphenylmethylthio)-thiazolo[4,5-d]pyrimidin-7-ylamino]-4-methyl-pentan-1-ol White solid (16 mg, 55% yield). MS 420 (M+1).

EXAMPLE 24

(R)-2-[2-Amino-5-(4-methoxyphenylmethylthio)-thiazolo[4,5-d]pyrimidin-7-ylamino]-4-methyl-pentan-1-ol White solid (13 mg, 45% yield). MS 420 (M+1).

EXAMPLE 25

(R)-2-[2-Amino-5-(2-fluoro-3-methylphenylmethylthio)-thiazolo[4,5-d]pyrimidin-7-ylamino]-4-methyl-pentan-1-ol White solid (11 mg, 40% yield). MS 422 (M+1).

EXAMPLE 26

(R)-2-[2-Amino-5-(2-fluoro-3-trifluoromethylphenylmethylthio)-thiazolo[4,5-d]pyrimidin-7-ylamino]-methyl-pentan-1-ol White solid (16 mg, 49% yield). MS 476 (M+1).

EXAMPLE 27

(R)-2-[2-Amino-5-(2-bromo-5-methylphenylmethylthio)-thiazolo[4,5-d]pyrimidin-7-ylamino]-4-methyl-pentan-1-ol White solid (14 mg, 43% yield). MS 482, 484 (M+1).

EXAMPLE 28

(R)-2-[2-Amino-5-(3-methoxycarbonylphenylmethylthio)-thiazolo[4,5-d]pyrimidin-7-ylamino]-4-methyl-pentan-1-ol White solid (13 mg, 44% yield). MS 448 (M+1).

EXAMPLE 29

(R)-2-[2-Amino-5-(4-trifluoromethylphenylmethylthio)-thiazolo[4,5-d]pyrimidin-7-ylamino]-4-methyl-pentan-1-ol White solid (15 mg, 58% yield). MS 458 (M+1).

EXAMPLE 30

(R)-2-[2-Amino-5-(2-trifluoromethylphenylmethylthio)-thiazolo[4,5-d]pyrimidin-7-ylamino]4-methyl-pentan-1-ol White solid (17 mg, 56% yield). MS 458 (M+1).

EXAMPLE 31

(R)-2-[2-Amino-5-(4-cyanophenylmethylthio)-thiazolo[4,5-d]pyrimidin-7-ylamino]-4-methyl-pentan-1-ol White solid (16 mg, 57% yield). MS 415 (M+1).

EXAMPLE 32

(R)-2-[2-Amino-5-(4-methylphenylmethylthio)-thiazolo[4,5-d]pyrimidin-7-ylamino]-4-methyl-pentan-1-ol White solid (14 mg, 52% yield). MS 404 (M+1).

EXAMPLE 33

(R)-2-[2-Amino-5-(3-methylphenylmethylthio)-thiazolo[4,5-d]pyrimidin-7-ylamino]-4-methyl-pentan-1-ol White solid (15 mg, 54% yield). MS 404 (M+1).

EXAMPLE 34

(R)-2-[2-Amino-5(2-cyanophenylmethylthio)-thiazolo[4,5-d]pyrimidin-7-ylamino]-4-methyl-pentan-1-ol White solid (16 mg, 58% yield). MS 415 (M+1).

EXAMPLE 35

(R)-2-[2-Amino-5-(2-methylphenylmethylthio)-thiazolo[4,5-d]pyrimidin-7-ylamino]-4-methyl-pentan-1-ol White solid (16 mg, 59% yield). MS 404 (M+1).

EXAMPLE 36

(R)-2-[2-Amino-5-(3-trifluoromethylphenylmethylthio)-thiazolo[4,5-d]pyrimidin-7-ylamino]-4-methyl-pentan-1-ol White solid (18 mg, 58% yield). MS 458 (M+1).

EXAMPLE 37

(R)-2-[2-Amino-5-(3-cyanophenylmethylthio)-thiazolo[4,5-d]pyrimidin-7-ylamino]-4-methyl-pentan-1-ol An amount of 30 mg of the product from Example 5, step (a), was used as starting material.
White solid (24 mg, 57% yield). MS 415 (M+1).

EXAMPLE 38

(R)-2-[2-Amino-5-(3-methyl-2-nitrophenylmethylthio)-thiazolo[4,5-d]pyrimidin-7-ylamino]-4-methyl-pentan-1-ol Pale yellow solid (10 mg, 32% yield). MS 449 (M+1).

EXAMPLE 39

N-(2-Amino-5-phenylmethylthio-thiazolo[4,5-d]pyrimidin-7-yl)-1-hydroxymethyl-cyclopentylamine Prepared according to the procedure in Example 1, from 5-phenylmethylthio-7-chloro-thiazolo[4,5-d]pyrimidin-2-ylamine and cycloleucinol.
Yellow solid (97 mg, 39% yield). MS 388 (M+1).

EXAMPLE 40

(±)-2-[2-Amino-5-(2,3-difluorophenylmethylthio)-thiazolo[4,5-d]pyrimidin-7-ylamino]-hexan-1-ol Prepared according to the procedure in Example 1, from 5-(2,3-difluorophenylmethylthio)-7-chloro-thiazolo[4,5-d]pyrimidin-2-ylamine (WO 00/09511) and DL-2-amino-1-hexanol, with triethylamine (one equivalent) added.
White solid (60 mg, 16% yield). MS 426 (M+1).

SCREENS

The pharmacological activity of compounds according to the invention was tested in the following screens.

Materials. Recombinant human fractalkine (hCX$_3$CL1) was purchased from PeproTech Inc., UK. Recombinant [$^{125}$I]-fractalkine (human), with a specific activity 2200 Ci/mmol, and [$^{35}$S]-GTPγS, with a specific activity of 1250 Ci/mmol at the calibration date, were purchased from NEN® Life Science Products, Inc., UK. Wheatgerm agglutinin (WGA) scintillation proximity assay.(SPA) beads were purchased from Amersham, UK. Ultima-Gold liquid scintillation cocktail was purchased from Packard Company, US. All other chemicals were of analytical grade.

Expression of mouse fractalkine receptor (mCX$_3$CR1). A Probe based on human and rat CX$_3$CR1 sequences was designed and utilised to screen a Life Technologies Super-Script™ mouse brain cDNA library. The clones isolated from the cDNA library are fill coding sequence and confirmed to be identical with the published mCX$_3$CR1 sequence (AC AF074912). The entire coding sequence was sub-cloned into the mammalian expression vector pGEN IRES-neo (ASTRAZENECA). Plasmid DNA was prepared using QIAGEN Plasmid Midi Kit and transfected into human embryonic kidney (HEK) 293 cells using calcium phosphate-precipitation protocol (Chen and Okayama, 1987, Mol. Cell. Biol. 7, 2745–2752). A stable clone was generated using geneticin (G418, 1 mg/ml) selection.

Cells were harvested in buffer containing 10 mM Tris-HCl, pH 7.4, 5 mM ethylenediaminetetra-acetic acid (EDTA) and 0.1 mg/ml bacitracin (a protease inhibitor) and centrifuged at 300×g for 10 min. Cell pellets were then resuspended in harvesting buffer, pooled and homogenised using Dounce homogeniser. Cell membranes were centrifuged at 48000×g for 10 min and then resuspended in harvesting buffer using Ultra-Turrax T8 (IKA Labortechnik, Germany). Protein concentration was determined in microtiter plates as described by Harrington (1990, Anal. Biochem. 186, 285–287). Membrane aliquots were stored at −70° C. Receptor expression was confirmed with [$^{125}$I]-fractalkine binding using whole cells.

SPA-Ligand Binding Assay. Competition binding assays were performed in white clear bottom 96well isoplates (Wallac, Finland) in a total volume of 100 μl/well. Each well contained 100 pM [$^{125}$I]-fractalkine, membrane equivalent to receptor concentration of 50 pM and 0.750 mg SPA-beads in assay buffer [50 mM Hepes-KOH, pH 7.4, 10 mM MgCl$_2$, 1 mM EDTA, 0.5% (w/v) gelatin]. Test compounds were pre-dissolved in DMSO and added to reach a final concentration of 10% (v/v) DMSO. The assay was initiated with the addition of membranes and incubated at room temperature for 2 h. Assay plates were counted in Microbeta Trilux 1450 (Wallac).

GTPγS Binding Assay. Fractalkine stimulates [$^{35}$S]-GTPγS binding to G-proteins in HEK293 cell membranes expressing mCX$_3$CR1. The ability of test compounds to inhibit fractalkine induced [$^{35}$S]-GTPγS binding was studied using mCX$_3$CR1/HEK293 membranes (20 μg/250 μl total volume). Reactions were performed in assay buffer containing 50 mM Tris-HCl, pH 7.4, 10 mM MgCl$_2$, 0.1% (w/v) gelatin and 3 μM GDP. Compound and membranes were pre-incubated for 20 min at 30° C. before addition of 300 pM fractalkine. After 30 min of further incubation, 0.15–0.20 nM [$^{35}$S]-GTPγS was added and the incubation was continued for 30 min. The reaction was terminated by rapid filtration through GF/B filters (Whatman Int. Ltd, UK) using Brandel cell-harvester (Biomedical R&D Laboratories, Maryland, US). Filters were washed four times with ice-cold buffer containing 50 mM Tris-HCl, pH 7.4 and 5 mM MgCl$_2$. Scintillation fluid (Packard Ultima-Gold, 4 ml) was added and the radioactivity was determined using Packard 2900TR liquid scintillation analyzer.

Results. When tested in the SPA-ligand binding assay, the compounds of Examples 1 to 40 gave $K_i$ values of less than 10 μM, indicating that they are expected to show useful therapeutic activity.

The invention claimed is:
1. A compound selected from:
R)-2-[5-phenylmethylthio-7-(1-hydroxymethyl-3-methyl-butylamino)-thiazolo[4,5-d]pyrimidin-2-ylamino] acetamide;
(R)-2-[5-phenylmethylthio-2-(piperidin-4-ylamino)-thiazolo[4,5-d]pyrimidin-7-ylamino]-4-methyl-pentan-1-ol;
(R)-2-[2-amino-5-(2-fluorophenylmethylthio)-thiazolo[4,5-d]pyrimidin-7-ylamino]-4-methyl-pentan-1-ol;
(R)-2-[2-amino-5-(2-chlirophenylmethylthio)-thiazolo[4,5-d]pyrimidin-7-ylamino]-4-methyl-pentan-1-ol;
(R)-2-[2-amino-5-(2-bromophenylmethylthio)-thiazolo[4,5-d]pyrimidin-7-ylamino]-4-methyl-pentan-1-ol;
(R)-2-[2-amino-5-(3-bromophenylmethylthio)-thiazolo[4,5-d]pyrimidin-7-ylamino]-4-methyl-pentan-1-ol;
(R)-2-[2-amino-5-(4-bromophenylmethylthio)-thiazolo[4,5-d]pyrimidin-7-ylamino]-4-methyl-pentan-1-ol;
(R)-2-[2-amino-5-(2-iodophenylmethylthio)-thiazolo[4,5-d]pyrimidin-7-ylamino]-4-methyl-pentan-1-ol;
(R)-2-[2-amino-5-(2,4-difluorophenylmethylthio)-thiazolo[4,5-d]pyrimidin-7-ylamino]-4-methyl-pentan-1-ol;
(R)-2-[2-amino-5-(2,5-difluorophenylmethylthio)-thiazolo[4,5-d]pyrimidin-7-ylamino]-4-methyl-pentan-1-ol;
(R)-2-[2-amino-5-(2,6-difluorophenylmethylthio)-thiazolo[4,5-d]pyrimidin-7-ylamino]-4-methyl-pentan-1-ol;
(R)-2-[2-amino-5-(3,4-difluorophenylmethylthio)-thiazolo[4,5-d]pyrimidin-7-ylamino]-4-methyl-pentan-1-ol;
(R)-2-[2-amino-5-(3,5-difluorophenylmethylthio)-thiazolo[4,5-d]pyrimidin-7-ylamino]-4-methyl-pentan-1-ol;
(R)-2-[-2-amino-5-(3-chloro-2-fluorophenylmethylthio)-thiazolo[4,5-d]pyrimidin-7-ylamino]-4-methyl-pentan-1-ol;
(R)-2-[-2-amino-5-(2-chloro-6-fluorophenylmethylthio)-thiazolo[4,5-d]pyrimidin-7-ylamino]-4-methyl-pentan-1-ol;
(R)-2-[-2-amino-5-(4-bromo-2-fluorophenylmethylthio)-thiazolo[4,5-d]pyrimidin-7-ylamino]-4-methyl-pentan-1-ol;
(R)-2-[-2-amino-5-(2-bromo-5-fluorophenylmethylthio)-thiazolo[4,5-d]pyrimidin-7-ylamino]-4-methyl-pentan-1-ol;
(R)-2-[2-amino-5-(2,3-dichlorophenylmethylthio)-thiazolo[4,5-d]pyrimidin-7-ylamino]-4-methyl-pentan-1-ol;
(R)-2-[2-amino-5-(2-chloro-4,5-methylenedioxyphenylmethylthio)-thiazolo [4,5-d]pyrimidin-7-ylamino]-4-methyl-pentan-1-ol;
(R)-2-[2-amino-5-(2-methoxyphenylmethylthio)thiazolo[4,5-d]pyrimidin-7-ylamino]-4-methyl-pentan-1-ol;
(R)-2-[2-amino-5-(3-methoxyphenylmethylthio)thiazolo[4,5-d]pyrimidin-7-ylamino]-4-methyl-pentan-1-ol;
(R)-2-[2-amino-5-(4-methoxyphenylmethylthio)thiazolo[4,5-d]pyrimidin-7-ylamino]-4-methyl-pentan-1-ol;
(R)-2-[2-amino-5-(2-fluoro-3-methylphenylmethylthio)-thiazolo[4,5-d]pyrimidin-7-ylamino]-4-methyl-pentan-1-ol;
(R)-2-[2-amino-5-(2-fluoro-3-trifluoromethylphenylmethylthio)-thiazolo [4,5-d]pyrimidin-7-ylamino]-4-methyl-pentan-1-ol;

(R)-2-[2-amino-5-(2-bromo-3-methylphenylmethylthio)-thiazolo[4,5-d]pyrimidin-7-ylamino]-4-methyl-pentan-1-ol;

(R)-2-[2-amino-5-(3-methoxyphenylmethylthio)thiazolo[4,5-d]pyrimidin-7-ylamino]-4-methyl-pentan-1-ol;

(R)-2-[2-amino-5-(4-trifluoromethylphenylmethylthio)-thiazolo[4,5-d]pyrimidin-7-ylamino]-4-methyl-pentan-1-ol;

(R)-2-[2-amino-5-(2-trifluoromethylphenylmethylthio)-thiazolo[4,5-d]pyrimidin-7-ylamino]-4-methyl-pentan-1-ol;

(R)-2-[2-amino-5-(4-cyanophenylmethylthio)-thiazolo[4,5-d]pyrimidin-7-ylamino]-4-methyl-pentan-1-ol;

(R)-2-[2-amino-5-(4-methylphenylmethylthio)-thiazolo[4,5-d]pyrimidin-7-ylamino]-4-methyl-pentan-1-ol;

(R)-2-[2-amino-5-(3-methylphenylmethylthio)-thiazolo[4,5-d]pyrimidin-7-ylamino]-4-methyl-pentan-1-ol;

(R)-2-[2-amino-5-(2-cyanophenylmethylthio)-thiazolo[4,5-d]pyrimidin-7-ylamino]-4-methyl-pentan-1-ol;

(R)-2-[2-amino-5-(2-methylphenylmethylthio)-thiazolo[4,5-d]pyrimidin-7-ylamino]-4-methyl-pentan-1-ol;

(R)-2-[2-amino-5-(3-trifluoromethylphenylmethylthio)-thiazolo[4,5-d]pyrimidin-7-ylamino]-4-methyl-pentan-1-ol;

(R)-2-[2-amino-5-(3-cyanophenylmethylthio)-thiazolo[4,5-d]pyrimidin-7-ylamino]-4-methyl-pentan-1-ol;

(R)-2-[2-amino-5-(3-methyl-2-nitrophenylmethylthio)-thiazolo[4,5-d]pyrimidin-7-ylamino]-4-methyl-pentan-1ol;

N-(2-amino-5-phenylmethylthio-thiazolo[4,5-d]pyrimidin-7-1-hydroxymethyl-cyclopentylamine;

(±)-2-[2-amino-5-(2,3-difluorophenylmethylthio)-thiazolo[4,5-d]pyrimidin-7-ylamino ]hexan-1-ol;

or a pharmaceutically acceptable salt, enantiomer or raccmate thereof.

* * * * *